United States Patent
Hatta (10) Patent No.: US 9,689,742 B2
(45) Date of Patent: Jun. 27, 2017

(54) ULTRAVIOLET-SENSITIVE SHEET, METHOD FOR MANUFACTURING ULTRAVIOLET-SENSING SHEET, AND METHOD FOR SENSING ULTRAVIOLET

(71) Applicant: FUJIFILM Corporation, Tokyo (JP)

(72) Inventor: Masahiro Hatta, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/829,964

(22) Filed: Aug. 19, 2015

(65) Prior Publication Data

US 2015/0355021 A1    Dec. 10, 2015

Related U.S. Application Data (63) Continuation of application No. PCT/JP2014/054420, filed on Feb. 25, 2014.

(30) Foreign Application Priority Data

Feb. 25, 2013  (JP) ................... 2013-035046
Feb. 24, 2014  (JP) ................... 2014-032536

(51) Int. Cl.
*G01J 1/50*  (2006.01)
*G01J 1/04*  (2006.01)
*G01J 1/42*  (2006.01)

(52) U.S. Cl.
CPC ............. *G01J 1/50* (2013.01); *G01J 1/0407* (2013.01); *G01J 1/429* (2013.01)

(58) Field of Classification Search
CPC ....................................................... G01J 1/50
See application file for complete search history.

(56) References Cited

U.S. PATENT DOCUMENTS

| 4,829,187 A | 5/1989 | Tomita et al. |
| 4,962,009 A * | 10/1990 | Washizu ............... G03C 1/002 430/138 |
| 2015/0355020 A1 | 12/2015 | Hatta |

FOREIGN PATENT DOCUMENTS

| EP | 1 997 428 A1 | 12/2008 |
| JP | 62-112020 A | 5/1987 |

(Continued)

OTHER PUBLICATIONS

International Preliminary Report on Patentability dated Sep. 3, 2015 issued by the International Bureau in counterpart International Application No. PCT/JP2014/054420.

(Continued)

*Primary Examiner* — Edwin Gunberg
(74) *Attorney, Agent, or Firm* — Sughrue Mion, PLLC (57) ABSTRACT

Provided an ultraviolet-sensing sheet that facilitates measurement of ultraviolet irradiance over a wide area, that is suitable in ultraviolet irradiance in a range from 1 to 1,000 $mJ/cm^2$, a method for manufacturing such an ultraviolet-sensing sheet, and a method for sensing ultraviolet. The ultraviolet-sensing sheet has a change in reflection density $\Delta D1$ of 0.2 or more over a range of cumulative illuminance 1 $mJ/cm^2$ or more and less than 10 $mJ/cm^2$, a change in reflection density $\Delta D2$ of 0.2 or more over a range of cumulative illuminance 10 $mJ/cm^2$ or more and less than 100 $mJ/cm^2$, and a change in reflection density $\Delta D3$ of 0.2 or more over a range of cumulative illuminance 100 $mJ/cm^2$ or more and 1,000 $mJ/cm^2$ or less, as measured at a wavelength of 365 nm when the ultraviolet-sensing sheet is irradiated with a high-pressure mercury lamp.

20 Claims, 2 Drawing Sheets

(56) References Cited

FOREIGN PATENT DOCUMENTS

| JP | 63-305189 | A | 12/1988 |
|---|---|---|---|
| JP | H 1-207741 | A | 8/1989 |
| JP | 1-272930 | A | 10/1989 |
| JP | 02-000044 | A | 1/1990 |
| JP | 3-19536 | B2 | 3/1991 |
| JP | 09-126887 | A | 5/1997 |
| JP | 10-122958 | A | 5/1998 |
| JP | 10-288552 | A | 10/1998 |
| JP | 2001-147154 | A | 5/2001 |
| JP | 2009-543057 | A | 12/2009 |
| WO | 2007/108322 | A1 | 9/2007 |
| WO | 2007/108332 | A1 | 9/2007 |
| WO | 2008/002743 | A1 | 1/2008 |

OTHER PUBLICATIONS

International Preliminary Report on Patentability dated Sep. 3, 2015 issued in International Application No. PCT/JP2014/054267.
Office Action dated Apr. 5, 2016, from the Japanese Patent Office in corresponding Japanese Patent Application No. 2014-032536.
International Search Report [PCT/ISA/210] dated May 13, 2014 in International Application No. PCT/JP2014/054267.
Written Opinion [PCT/ISA/237] dated May 13, 2014 in International Application No. PCT/JP2014/054267.
Office Action dated May 20, 2016, from the State Intellectual Property Office of People's Republic of China in Chinese Application No. 201480009998.X.
Shigemitsu Morita, "Development of microcapsule UV actinometer", Journal of Azabu University, vol. 13, No. 14, Mar. 31, 2007, pp. 229-235.
International Search Report of PCT/JP2014/054420 dated May 27, 2014 [PCT/ISA/210].
Written Opinion of PCT/JP2014/054420 dated May 27, 2014 [PCT/ISA/237].
Office Action dated Apr. 5, 2016 from the Japanese Patent Office in Japanese Application No. 2013-035047.
Office Action dated Nov. 29, 2016 from the Japanese Patent Office in Japanese Application No. 2013-035047.
Office Action dated Jul. 18, 2016 from the State Intellectual Property Office of the P.R.C. in counterpart Chinese Application No. 201480009635.6.
Office Action dated Jun. 7, 2016, from the Japanese Patent Office in counterpart Japanese Application No. 2014-032536.
Office Action dated Feb. 7, 2017, from the Japanese Patent Office in counterpart Japanese Application No. 2014-032536.
Communication dated Mar. 3, 2017, from the State Intellectual Property Office of the P.R.C., in counterpart Chinese application No. 201480009635.6.

* cited by examiner

ULTRAVIOLET-SENSITIVE SHEET, METHOD FOR MANUFACTURING ULTRAVIOLET-SENSING SHEET, AND METHOD FOR SENSING ULTRAVIOLET

CROSS-REFERENCE TO RELATED APPLICATIONS

This application is a Continuation of PCT International Application No. PCT/JP2014/054420 filed on Feb. 25, 2014, which claims priority under 35 U.S.C §119(a) to Japanese Patent Application No. 2013-035046 filed on Feb. 25, 2013, and Japanese Patent Application No. 2014-032536 filed on Feb. 24, 2014. The above application is hereby expressly incorporated by reference, in its entirety, into the present application.

TECHNICAL FIELD

The present invention relates to ultraviolet-sensing sheets, methods for manufacturing ultraviolet-sensing sheets, and methods for sensing ultraviolet.

BACKGROUND ART

A measurement of an ultraviolet dose is used in various fields, for example, ultraviolet dosimeters are used to measure the ultraviolet dose of an object irradiated with ultraviolet radiation from an ultraviolet irradiation system for curing ultraviolet-curable resins.

Commonly known ultraviolet dosimeters are semiconductor photovoltaic devices, which are expensive and not readily portable. Simpler and inexpensive known tools are photochromic cards, which change color reversibly in response to ultraviolet. Although photochromic cards can be used to determine the ultraviolet intensity during irradiation, the cumulative illuimance of ultraviolet cannot be determined.

For example, Patent document 1 proposes a method for measuring cumulative irradiance with allochroic materials.

Also proposed are a method for quantitatively determining ultraviolet dose using photosensitive paper (see Patent document 2) and a method utilizing oxidative coloration of leuco dyes (see Patent document 3).

CITATION LIST

Patent Literature

Patent document 1: Japanese Unexamined Patent Application Publication No. 10-288552
Patent document 2: Japanese Unexamined Patent Application Publication No. 10-122958
Patent document 3: Japanese Unexamined Patent Application Publication No. 62-112020

SUMMARY OF INVENTION

Technical Problem

Unfortunately, the method in Patent document 1 is not suitable for quantitative determination because of insufficient sensitivity.

The method in Patent document 2 has several disadvantages. For example, this method requires a measuring instrument and a complicated procedure, cannot readily quantitatively determine the ultraviolet dose since no gradations of color are available, and requires careful handling of the results, which are susceptible to external light after ultraviolet dosimetry.

The method in patent document 3 has several disadvantages. For example, this method cannot readily quantitatively determine the ultraviolet dose since no gradations of color are available and yields results with instable images, which are susceptible to external light after ultraviolet dosimetry.

Those methods are also not suitable for ultraviolet irradiance in the range from 100 to 1,000 $mJ/cm^2$, which is most widely used in manufacturing processes involving the use of ultraviolet curing.

In view of the foregoing disadvantages, an object of the present invention is to provide an ultraviolet-sensing sheet that facilitates measurement of ultraviolet irradiance over a wide area, that is suitable in ultraviolet irradiance in a range from 1 to 1,000 $mJ/cm^2$, a method for manufacturing such an ultraviolet-sensing sheet, and a method for sensing ultraviolet.

Solution to Problem

The inventor has discovered that an ultraviolet-sensing sheet has a continuous color development depending on the cumulative illuminance of ultraviolet if the ultraviolet-sensing sheet has a change in reflection density $\Delta D1$ of 0.2 or more over a range of cumulative illuminance 1 $mJ/cm^2$ or more and less than 10 $mJ/cm^2$, a change in reflection density $\Delta D2$ of 0.2 or more over a range of cumulative illuminance 10 $mJ/cm^2$ or more and less than 100 $mJ/cm^2$, and a change in reflection density $\Delta D3$ of 0.2 or more over a range of cumulative illuminance 100 $mJ/cm^2$ or more and 1,000 $mJ/cm^2$ or less, as measured at a wavelength of 365 nm when the ultraviolet-sensing sheet is irradiated with a high-pressure mercury lamp, and thereby have completed the present invention.

Means for solving the problem is a means below <1>, preferably, it is a means of following <2> to <13>.

<1> An ultraviolet-sensing sheet which has a change in reflection density $\Delta D1$ of 0.2 or more in a range of cumulative illuminance of 1 $mJ/cm^2$ or more and less than 10 $mJ/cm^2$, a change in reflection density $\Delta D2$ of 0.2 or more in a range of cumulative illuminance of 10 $mJ/cm^2$ or more and less than 100 $mJ/cm^2$, and a change in reflection density $\Delta D3$ of 0.2 or more in a range of cumulative illuminance of 100 $mJ/cm^2$ or more and 1,000 $mJ/cm^2$ or less, as measured at a wavelength of 365 nm when the ultraviolet-sensing sheet is irradiated with a high-pressure mercury lamp.

<2> The ultraviolet-sensing sheet according to <1>, wherein the ultraviolet-sensing sheet comprises an ultraviolet-sensing layer comprising a capsule containing a photo-oxidant and a leuco dye capable of developing color by the photo-oxidant, a mass ratio of the photo-oxidant and the leuco dye is 0.2 to 1.0:1, and the leuco dye is present in an amount of 0.1 to 1.0 g per 1 $m^2$ of a surface area of the ultraviolet-sensing layer.

<3> The ultraviolet-sensing sheet according to <1> or <2>, wherein the photo-oxidant has a molar absorption coefficient $\epsilon$ of 2,000 or less at a wavelength of 350 nm and a molar absorption coefficient $\epsilon$ of 10,000 or more at a wavelength of 250 nm.

<4> The ultraviolet-sensing sheet according to any one of <1> to <3>, wherein the capsule is a microcapsule.

<5> The ultraviolet-sensing sheet according to any one of <1> to <4>, wherein the leuco dye is an aminoarylmethane.

<6> The ultraviolet-sensing sheet according to any one of <1> to <5>, wherein the ultraviolet-sensing sheet has a cumulative illuminance of from 1 to 1,000 mJ/cm$^2$ as measured at a wavelength of 365 nm when the ultraviolet-sensing sheet is irradiated with a high-pressure mercury lamp.

<7> The ultraviolet-sensing sheet according to any one of <1> to <6>, further comprising a support having the ultraviolet-sensing layer thereon.

<8> The ultraviolet-sensing sheet according to <7>, wherein the support is a plastic film.

<9> The ultraviolet-sensing sheet according to <7> or <8>, further comprising a reflective layer between the support and the ultraviolet-sensing layer or on a surface of the support, the surface being away from the ultraviolet-sensing layer.

<10> The ultraviolet-sensing sheet according to <9>, wherein the reflective layer is disposed between the support and the ultraviolet-sensing layer.

<11> The ultraviolet-sensing sheet according to any one of <1> to <10>, wherein the ultraviolet-sensing layer further comprises a reductant.

<12> A method for manufacturing the ultraviolet-sensing sheet according to any one of <1> to <11>,
the method comprising applying to a support an ultraviolet-sensing layer composition comprising a capsule containing a photo-oxidant and a leuco dye capable of developing color by the photo-oxidant, and a mass ratio of the photo-oxidant and the leuco dye is 0.2 to 1.0:1,
and the leuco dye is present in an amount of 0.1 to 1.0 g per 1 m$^2$ of the surface area of the support.

<13> A method for sensing ultraviolet using the ultraviolet-sensing sheet according to any one of <1> to <11>.

Advantageous Effects of Invention

The present invention provides an ultraviolet-sensing sheet that facilitates ultraviolet irradiance over a wide area, that is effective in ultraviolet irradiance in a range from 1 to 1,000 mJ/cm$^2$, a method for manufacturing such an ultraviolet-sensing sheet, and a method for sensing ultraviolet.

DESCRIPTION OF EMBODIMENTS

The present invention will be explained in detail below. As used herein, each numerical range expressed by two values on both sides of "to" is used to mean the range including the values indicated before and after "to" as lower and upper limits.

<Ultraviolet-Sensing Sheet>

An ultraviolet-sensing sheet according to the present invention, the ultraviolet-sensing sheet has a change in reflection density $\Delta D1$ of 0.2 or more in a range of cumulative illuminance of 1 mJ/cm$^2$ or more and less than 10 mJ/cm$^2$, a change in reflection density $\Delta D2$ of 0.2 or more in a range of cumulative illuminance of 10 mJ/cm$^2$ or more and less than 100 mJ/cm$^2$, and a change in reflection density $\Delta D3$ of 0.2 or more in a range of cumulative illuminance of 100 mJ/cm$^2$ or more and 1,000 mJ/cm$^2$ or less, as measured at a wavelength of 365 nm when the ultraviolet-sensing sheet is irradiated with a high-pressure mercury lamp.

Figure 1:
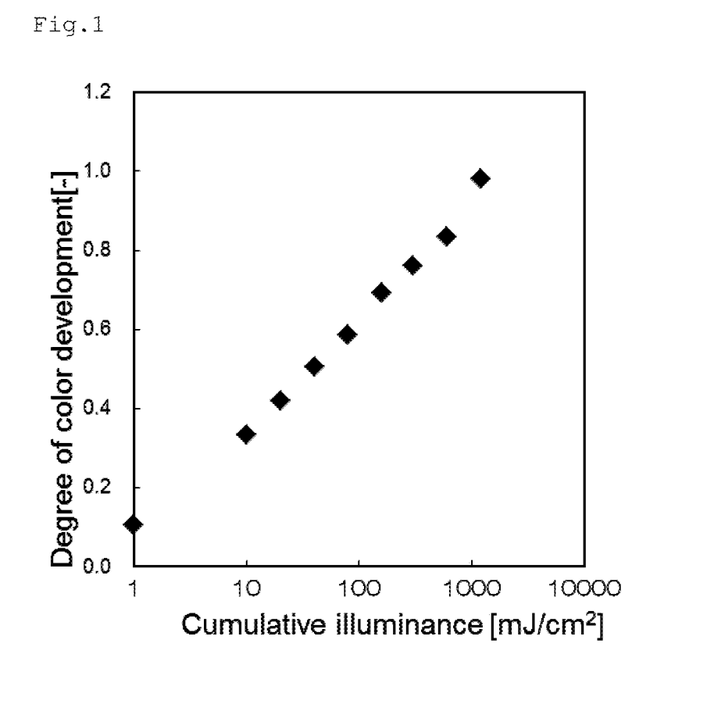
FIG. 1 is a graph showing the degree of developing color of the present invention.

An ultraviolet-sensing sheet satisfying the above requirements can respond sensitively to ultraviolet and sense ultraviolet. In particular, when the sheet is irradiated with a high-pressure mercury lamp, the degree of color development of the sheet according to the present invention vary depending on the irradiance measured at a wavelength of 365 nm, and thus can effectively determine the ultraviolet irradiance. As used herein, the term "high-pressure mercury lamp" refers to, for example, a high-pressure ultraviolet lamp available from Ushio Inc. FIG. 1 is a graph showing the degree of color development of the ultraviolet-sensing sheet according to the present invention, where the vertical axis is a logarithmic of the degree of color development, and the horizontal axis is a cumulative illuminance of ultraviolet. FIG. 1 demonstrates that the present invention can has a continuous color development on the cumulative illuminance of ultraviolet, thereby sensitively detecting ultraviolet radiation. In particular, the present invention can effectively detect ultraviolet radiation in a range of cumulative illuminance of ultraviolet of 1 to 1,000 mJ/cm$^2$.

Light sources other than high-pressure mercury lamps can also be used in the present invention. Examples of other light sources include metal halide lamps, ultraviolet-LED lamps, low-pressure mercury lamps, and ultraviolet lasers.

The sheet according to the present invention preferably has a change in reflection density $\Delta D1$ of 0.2 or more, more preferably 0.25 or more, in a range of cumulative illuminance of 1 mJ/cm$^2$ or more and less than 10 mJ/cm$^2$, a change in reflection density $\Delta D2$ of 0.2 or more, more preferably 0.25 or more, in a range of cumulative illuminance of 10 mJ/cm$^2$ or more and less than 100 mJ/cm$^2$, and a change in reflection density $\Delta D3$ of 0.2 or more, more preferably 0.25 or more, in a range of cumulative illuminance of 100 mJ/cm$^2$ or more and 1,000 mJ/cm$^2$ or less, when measured at a wavelength of 365 nm. Preferably, the sheet according to the present invention has a change in reflection density of 0.4 or less, although no critical upper limit is defined.

For example, the sheet according to the present invention may have a change in reflection density $\Delta D1$ of 0.21 to 0.36, a change in reflection density $\Delta D2$ of 0.22 to 0.29, and a change in reflection density $\Delta D3$ of 0.21 to 0.29.

The term "change in reflection density" refers to the color change after an irradiation illuminance with ultraviolet to before a predetermined cumulative illuminance; specifically, it can be measured with a reflection densitometer (X-Rite 310, X-Rite Inc.).

If the changes in reflection densities $\Delta D1$ to $\Delta D3$ fall within the above ranges, the ultraviolet-sensing sheet according to the present invention can continuously develop color depending on the cumulative ultraviolet illuminance, thereby sensitively sensing ultraviolet radiation.

Such effective sensing of ultraviolet is accomplished by the ultraviolet-sensing layer. The ultraviolet-sensing layer used in the present invention contains capsules containing a photo-oxidant and a leuco dye capable of developing color by the photo-oxidant a mass ratio of the photo-oxidant and the leuco dye is 0.2 to 1.0:1, and the leuco dye being present in an amount of 0.1 to 1.0 g per 1 $m^2$ of the surface area of the ultraviolet-sensing layer. As the ultraviolet dose increases, the photo-oxidant generates a larger number of radicals, and accordingly, a larger amount of leuco dye reacts with the radicals. The color density thus increases with the ultraviolet dose. This allows ultraviolet to be detected in the form of more precise gradations.

The ultraviolet sensing mechanism according to the present invention will now be described with reference to FIGS. 2 and 3. It should be understood that the drawings are not intended to limit the present invention.

Figure 2:
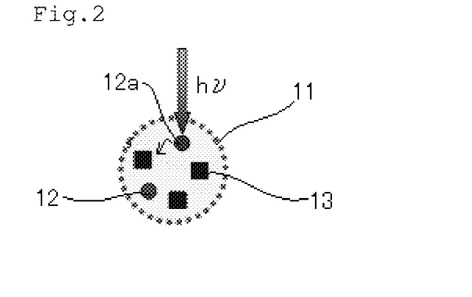
FIG. 2 is a schematic view of an example capsule for use in the present invention.
Figure 3:
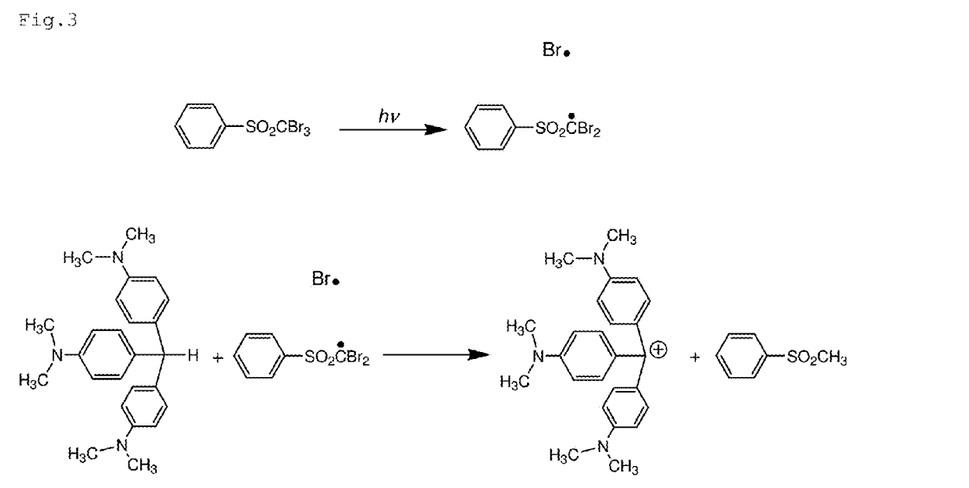
FIG. 3 illustrates an example reaction scheme of a photo-oxidant and a leuco dye.

FIG. 2 is a schematic view of an example capsule for use in the present invention. As shown in FIG. 2, the capsule 11 contains a photo-oxidant 12 and a leuco dye 13. FIG. 3 illustrates an example reaction scheme of the photo-oxidant and the leuco dye.

As shown in FIG. 2, upon ultraviolet irradiation, the photo-oxidant 12 in the capsule 11 absorbs ultraviolet radiation hυ. The photo-oxidant 12 absorbed ultraviolet radiation hυ is activated (an activated photo-oxidant 12a) to generate radicals (FIG. 3). As the ultraviolet dose increases, the photo-oxidant 12 generates a larger number of radicals, and accordingly, a larger amount of leuco dye 13 reacts with the resulting radicals. For example, the photo-oxidant and the leuco dye may be present in a predetermined mass ratio in the ultraviolet-sensing sheet according to the present invention, and the leuco dye may be present in a predetermined amount. This allows the color density to change continuously depending on the ultraviolet dose, as shown in FIG. 1, and thus allows the ultraviolet dose to be visually determined.

Specific examples of photo-oxidants and leuco dyes and the contents thereof will be described in further detail later.

<<Structure of Ultraviolet-Sensing Sheet>>

Figure 4:
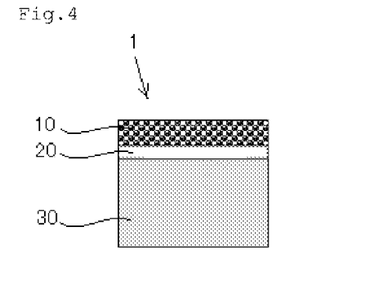
FIG. 4 is a schematic sectional view of an example ultraviolet-sensing sheet according to the present invention.

The structure of the ultraviolet-sensing sheet according to the present invention will now be described. FIG. 4 is a schematic sectional view of an example ultraviolet-sensing sheet according to the present invention. The ultraviolet-sensing sheet 1 according to the present invention includes an ultraviolet-sensing layer 10, a support 30 supporting the ultraviolet-sensing layer 10, and an optional reflective layer 20 between the support 30 and the ultraviolet-sensing layer 10. The ultraviolet-sensing layer 10 contains capsules dispersed therein. As illustrated in FIG. 2, each capsule contains a photo-oxidant and a leuco dye.

Figure 5:
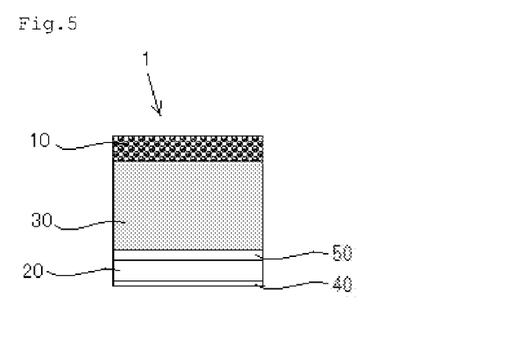
FIG. 5 is a schematic sectional view of an example ultraviolet-sensing kit according to the present invention.

FIG. 5 illustrates another example ultraviolet-sensing sheet according to the present invention. The ultraviolet-sensing sheet 1 according to this embodiment includes an ultraviolet-sensing layer 10, a support 30 supporting the ultraviolet-sensing layer 10, and an optional reflective layer 20 under the lower surface of the support 30, the lower surface being away from the ultraviolet-sensing layer 10. A glossy layer 40 may be disposed on a surface of the reflective layer 20, the surface being away from the support 30. The reflective layer 20 may be formed on an adhesion layer 50 provided on the support.

According to the embodiment illustrated in FIG. 5, the reflective layer 20 disposed on the lower surface, away from the ultraviolet-sensing layer 10, of the support 30 can more effectively reduce curling, for example, the height of rising at the four corners, at low humidity. According to the embodiment illustrated in FIG. 5, the glossy layer can be formed on the reflective layer to enhance the distinguishability between the front and back surfaces.

The ultraviolet-sensing sheet according to the present invention may be a film having a thickness of 200 µm or less or may be a sheet having a thickness of more than 200 µm. For example, the ultraviolet-sensing sheet according to the present invention may have a thickness of 5 to 250 µm, more specifically, 25 to 150 µm. The ultraviolet-sensing sheet according to the present invention may also be a rolled film.

The individual layers will now be described.

<<<Ultraviolet-Sensing Layer>>>

The ultraviolet-sensing layer used in the present invention contains capsules containing a photo-oxidant and a leuco dye capable of development color by the photo-oxidant in a predetermined ratio. The leuco dye is present in the ultraviolet-sensing layer used in the present invention in an amount of 0.1 to 1.0 g, preferably 0.15 to 0.8 g, more preferably 0.2 to 0.5 g, per 1 $m^2$ of a surface area of the ultraviolet-sensing layer. By setting to be such a range, the photo-oxidant more effectively responds to the ultraviolet irradiance, to thereby more sensitively develop color. The capsules will be described in further detail later.

The ultraviolet-sensing layer typically contains a binder in which the capsules are dispersed and may optionally contain other additives. Examples of binders include emulsions of various polymers such as poly(vinyl alcohol), methyl cellulose, carboxymethyl cellulose, hydroxypropyl cellulose, gum arabic, gelatin, polyvinylpyrrolidone, casein, styrene-butadiene latex, acrylonitrile-butadiene latex, poly(vinyl acetate), polyacrylates, and ethylene-vinyl acetate copolymers. The binder is used in an amount of 0.1 to 5 $g/m^2$ on a solid basis.

In addition to the leuco dye and the photo-oxidant contained in the capsules, the ultraviolet-sensing layer may further contain other components such as sensitizers, reductants, antioxidants, and surfactants. Several additives such as sensitizers, reductants, and surfactants are disclosed in Japanese Unexamined Patent Application Publication No. 1-207741 at page 9, lower left column, to page 10, upper left column, and in Japanese Unexamined Patent Application Publication No. 2004-233614 at paragraphs 0038, 0039, and 0048 to 0059, the entire disclosures of which are incorporated herein by reference.

The ultraviolet-sensing layer may have any thickness, but preferably a thickness of 3 to 30 µm, more preferably 10 to 20 µm, even more preferably 12 to 17 µm.

[Capsules]

The capsules present in the ultraviolet-sensing layer used in the present invention contain the photo-oxidant and the leuco dye in a predetermined mass ratio. The photo-oxidant and the leuco dye are present in the capsules in a mass ratio of 0.2 to 1.0:1, preferably 0.3 to 0.8:1, more preferably 0.4 to 0.7:1. By adding to be such a mass ratio, the photo-oxidant more effectively responds to the ultraviolet irradiance, to thereby more sensitively develop color. Preferably, the average mass ratio of the photo-oxidant to the leuco dye in each capsule falls within the above ranges; however, the effect of the present invention are achieved if the average mass ratio of the photo-oxidant to the leuco dye per unit area of the ultraviolet-sensing layer falls within the above ranges.

The capsules used in the present invention prevent contact between the materials inside and outside the capsules at room temperature under the barrier function of the shell wall and exhibit increased material permeability only when heated to a certain temperature or higher.

The permeation onset temperature can be controlled by selecting a suitable combination of a shell wall material, a capsule core material, and additives. The permeation onset temperature corresponds to the glass transition temperature of the shell wall. Specific compositions are illustrated in Japanese Unexamined Patent Application Publication Nos. 59-190886 and 60-242094, the entire disclosures of which are incorporated herein by reference.

To control the glass transition temperature of the shell wall itself, the type of shell-wall forming agent must be changed. Examples of microcapsule shell wall materials usable in the present invention include polyurethanes, polyureas, polyesters, polycarbonates, urea-formaldehyde resins, melamine-formaldehyde resins, polystyrene, styrene-methacrylate copolymers, gelatin, polyvinylpyrrolidone, and poly(vinyl alcohol). These polymeric materials can be used in combination. In the present invention, preferred among the above polymeric materials are polyurethanes, polyureas, polyamides, polyesters, and polycarbonates, more preferably polyurethanes and polyureas.

The capsules used in the present invention are preferably formed by emulsifying a core material containing the reactants, such as the leuco dye and the photo-oxidant, and then encapsulating the oil droplets with walls of a polymeric material. The reactant that forms the polymeric material may be added inside and/or outside the oil droplets. Details of preferred capsules for use in the present invention, including preferred methods for manufacturing such capsules, are disclosed in the specifications of U.S. Pat. Nos. 3,726,804 and 3,796,696, the entire disclosures of which are incorporated herein by reference.

For example, if polyurethaneurea is used as the shell wall material, a polyisocyanate and a second material (e.g., a polyol) reactive therewith to form the shell wall are mixed in an aqueous phase or in the oily liquid to be encapsulated. The mixture is emulsified in water and is heated to induce a polymerization reaction at oil droplet interfaces, thereby forming a shell wall. Polyurea is formed, for example, if the second material is polyamine or if no material is added.

Polyisocyanates and polyols and polyamines reactive therewith (second materials) for use herein are disclosed in the specifications of U.S. Pat. Nos. 3,281,383, 3,773,695, and 3,793,268, Japanese Examined Patent Application Publication Nos. 48-40347, 49-24159, and 48-84086, and Japanese Unexamined Patent Application Publication No. 48-80191, the entire disclosures of which are incorporated herein by reference.

Examples of polyisocyanates include diisocyanates, such as m-phenylene diisocyanate, p-phenylene diisocyanate, 2,6-tolylene diisocyanate, 2,4-tolylene diisocyanate, naphthalene 1,4-diisocyanate, diphenylmethane 4,4-diisocyanate, 3,3'-dimethoxy-4,4'-biphenyl diisocyanate, 3,3'-dimethyldiphenylmethane 4,4'-diisocyanate, xylylene 1,4-diisocyanate, 4,4'-diphenylpropane diisocyanate, trimethylene diisocyanate, hexamethylene diisocyanate, propylene 1,2-diisocyanate, butylene 1,2-diisocyanate, cyclohexylene 1,2-diisocyanate, and cyclohexylene 1,4-diisocyanate; triisocyanates, such as 4,4',4'-triphenylmethane triisocyanate and toluene 2,4,6-triisocyanate; tetraisocyanates, such as 4,4'-dimethyldiphenylmethane 2,2',5,5'-tetraisocyanate; and isocyanate prepolymers, such as adducts of hexamethylene diisocyanate with trimethylolpropane, adducts of 2,4-tolylene diisocyanate with trimethylolpropane, adducts of xylylene diisocyanate with trimethylolpropane, and adducts of tolylene diisocyanate with hexanetriol. Examples of commercially available polyisocyanates include the TAKENATE series, such as TAKENATE D-110N (Mitsui Chemicals, Inc.).

Examples of polyols include aliphatic polyalcohols, aromatic polyalcohols, hydroxy polyesters, and hydroxy polyalkylene ethers.

Specific examples include polyols disclosed in Japanese Unexamined Patent Application Publication No. 60-49991, including ethylene glycol, 1,3-propanediol, 1,4-butanediol, 1,5-pentanediol, 1,6-hexanediol, 1,7-heptanediol, 1,8-octanediol, propylene glycol, 2,3-dihydroxybutane, 1,2-dihydroxybutane, 1,3-dihydroxybutane, 2,2-dimethyl-1,3-propanediol, 2,4-pentanediol, 2,5-hexanediol, 3-methyl-1,5-pentanediol, 1,4-cyclohexanedimethanol, dihydroxycyclohexane, diethylene glycol, 1,2,6-trihydroxyhexane, 2-phenylpropylene glycol, 1,1,1-trimethylolpropane, hexanetriol, pentaerythritol, pentaerythritol ethylene oxide adducts, glycerol ethylene oxide adducts, glycerol, 1,4-di(2-hydroxyethoxy)benzene, condensates of aromatic polyalcohols such as resorcinol dihydroxyethyl ether with alkylene oxides, p-xylylene glycol, m-xylylene glycol, α,α'-dihydroxy-p-diisopropylbenzene, 4,4'-dihydroxydiphenylmethane, 2-(p,p'-dihydroxydiphenylmethyl)benzyl alcohol, adducts of bisphenol A with ethylene oxide, and adducts of bisphenol A with propylene oxide. The polyol is preferably used in an amount of 0.02 to 2 mol of hydroxyl group per 1 mol of isocyanate group.

Examples of polyamines include ethylenediamine, trimethylenediamine, tetramethylenediamine, pentamethylenediamine, hexamethylenediamine, p-phenylenediamine, m-phenylenediamine, piperazine, 2-methylpiperazine, 2,5-dimethylpiperazine, 2-hydroxytrimethylenediamine, diethylenetriamine, triethylenetriamine, triethylenetetramine, diethylaminopropylamine, tetraethylenepentamine, and adducts of epoxy compounds with amines. Polyisocyanates can be reacted with water to form polymeric materials.

The organic solvent used to form oil droplets may be selected from common high-boiling oils, including phosphates, such as tricresyl phosphate; phthalates, such as dibutyl phthalate; acrylates; methacrylates; other carboxylates; fatty acid amides, such as N,N-diethyldodecanamide; alkylated biphenyls; alkylated terphenyls; chlorinated paraffin; alkylated naphthalenes; and diarylethanes. Specific examples include those disclosed in Japanese Unexamined Patent Application Publication Nos. 60-242094 and 63-045084, the entire disclosures of which are incorporated herein by reference.

In the present invention, the above organic solvents may be used in combination with cosolvents as low-boiling dissolution aids. Examples of such cosolvents include ethyl acetate, isopropyl acetate, butyl acetate, and methylene chloride.

The water-soluble polymer present as a protective colloid in the aqueous phase to be mixed with the oil phase may be selected from known anionic polymers, nonionic polymers, and amphoteric polymers, preferably from poly(vinyl alcohol), gelatin, and cellulose derivatives.

A surfactant may be incorporated into the aqueous phase. The surfactant incorporated into the aqueous phase may be selected from anionic and nonionic surfactants that do not react with the protective colloid to cause precipitation or aggregation.

Preferred examples of surfactants include sodium alkylbenzenesulfonates (e.g., sodium lauryl sulfate), dioctyl sodium sulfosuccinate, and poly(alkylene glycol)s (e.g., poly(oxyethylene nonylphenyl ether)).

The capsules used in the present invention are typically microcapsules having an average particle size of micrometer order. Preferably, the capsules have an average particle size of 0.1 to 100 µm, more preferably 0.3 to 10 µm, even more preferably 0.5 to 5 µm. Capsules having an average particle size of 0.1 µm or more can more stably protect the core material therein. Capsules having an average particle size of 100 μm or less provides a chromogenic material with a higher resolution.

The term "average particle size" refers to the volume average particle size measured with an LA950 laser scattering particle size distribution analyzer (HORIBA, Ltd.).

[Leuco Dye]

The leuco dye used in the present invention can react with the photo-oxidant to give a color. The leuco dye is a reduced dye that has one or two hydrogen atoms and that loses or gains electrons to form a colored dye. Any leuco dye that is substantially colorless or slightly colored before losing electrons can be selected to achieve photo-oxidative coloration. A single leuco dye or a mixture of leuco dyes may be used.

Examples of the leuco dyes for use in the present invention include those disclosed in, for example, the specification of U.S. Pat. No. 3,445,234, including (a) aminotriarylmethanes, (b) aminoxanthines, (C) aminothioxanthines, (d) amino-9,10-dihydroacridines, (e) aminophenoxazines, (f) aminophenothiazines, (g) aminodihydrophenazines, (h) aminodiphenylmethanes, (i) leuco indamines, (j) aminohydrocinnamic acids (cyanoethanes, leuco methines), (k) hydrazines, (l) leuco indigoid dyes, (m) amino-2,3-dihydroanthraquinones, (n) tetrahalo-p,p'-biphenols, (o) 2-(p-hydroxyphenyl)-4,5-diphenylimidazoles, and (p) phenethylanilines. Of these leuco dyes, the leuco dyes (a) to (i) lose one hydrogen atom to form a colored dye, whereas the leuco dyes (j) to (p) lose two hydrogen atoms to form a dye.

In particular, aminoarylmethanes are preferred, and aminotriarylmethanes are more preferred. Preferred aminotriarylmethanes generally include aminotriarylmethanes and acid salts thereof where at least two of the aryl groups are phenyl groups each having:

(a) an $R^1R^2N$-substituent at the para position to the bond to the methane carbon atom where $R^1$ and $R^2$ are each a moiety selected from hydrogen, $C_1$ to $C_{10}$ alkyl group, 2-hydroxyethyl group, 2-cyanoethyl group, and benzyl group; and (b) a substituent at an ortho position to the methane carbon atom, where the substituent is selected from lower alkyl group (i.e., having 1 to 4 carbon atoms), lower alkoxy group (i.e., having 1 to 4 carbon atoms), fluorine atom, chlorine atom, and bromine atom, and; the third aryl group (i.e., the remaining aryl group) may be the same as or different from the first and second aryl groups and, when different, is selected from (a) phenyl group optionally substituted by lower alkyl group, lower alkoxy group, chlorine atom, diphenylamino group, cyano group, nitro group, hydroxy group, fluorine atom, bromine atom, alkylthio group, arylthio group, thioester group, alkylsulfonic acid group, arylsulfonic acid group, sulfonic acid group, sulfonamide group, alkylamide group, arylamide group, or the like; (b) naphthyl group optionally substituted by amino group, di-lower-alkylamino group, or alkylamino group; (c) pyridyl group optionally substituted by alkyl group; (d) quinolyl group; and (e) indolinylidene group optionally substituted by alkyl group.

Preferably, $R^1$ and $R^2$ are each hydrogen atom or $C_1$ to $C_4$ alkyl group. Most preferably, all three aryl groups are the same.

Specific examples of such leuco dyes include tris(4-dimethylaminophenyl)methane, tris(4-diethylaminophenyl) methane, bis(4-diethylaminophenyl)-(4-diethylamino-2-methylphenyl)methane, bis(4-diethylamino-2-methylphenyl)-(4-diethylaminophenyl)methane, bis(1-ethyl-2-methylindol-3-yl)-phenylmethane, 2-N-(3-trifluoromethylphenyl)-N-ethylamino-6-diethylamino-9-(2-methoxycarbonylphenyl)xanthene, 2-(2-chlorophenyl)amino-6-dibutylamino-9-(2-methoxycarbonylphenyl) xanthene, 2-dibenzylamino-6-diethylamino-9-(2-methoxycarbonylphenyl)xanthene, benzo[a]-6-N,N-diethylamino-9,2-methoxycarbonylphenyl)xanthene, 2-(2-chlorophenyl)-amino-6-dibutylamino-9-(2-methylphenylcarboxamidophenyl)xanthene, 3,6-dimethoxy-9-(2-methoxycarbonyl)phenylxanthene, benzoyl leuco methylene blue, and 3,7-bis-diethylaminophenoxazine. Examples of commercially available leuco dyes include leuco crystal violet (LCV, Yamada Chemical Co., Ltd.).

[Photo-Oxidant]

The photo-oxidant used in the present invention is activated by ultraviolet to generate radicals. The use of the photo-oxidant allows the color density to change continuously depending on the ultraviolet irradiance and thus allows the ultraviolet dose to be visually determined.

The photo-oxidant used in the present invention may have any ε value at a wavelength of 350 nm, but preferably an ε value of 2,000 or less, more preferably 1,000 or less, even more preferably 500 or less. For example, the photo-oxidant may have an s value of 320 or less, or 280 or less. The photo-oxidant used in the present invention may have any ε value at a wavelength of 250 nm, but preferably an s value of 10,000 or more, more preferably 11,000 or more, even more preferably 12,000 or more. For example, the photo-oxidant may have an ε value of 12,630 or more, or 12,740 or more. The use of such photo-oxidants further enhances the ultraviolet sensitive ability of the ultraviolet-sensing sheet according to the present invention. As used herein, the symbol "ε" refers to the molar absorption coefficient of the photo-oxidant, which can be measured, for example, with an ultraviolet spectrophotometer.

The photo-oxidant used in the present invention is preferably selected from photo-oxidants represented by Formulae (1) to (7) below. These photo-oxidants may be used alone or in mixture.

[Chem. 1]

General Formula (1)

where A, B, and D are each independently a carbon ring or heteroaryl group unsubstituted or substituted by a substituent that does not interfere with dissociation of the dimer into imidazolyl groups or oxidation of the leuco dye.

The symbols A, B, and D are each independently a carbon ring or heteroaryl group unsubstituted or substituted by a substituent that does not interfere with dissociation of the dimer into imidazolyl groups or oxidation of the leuco dye.

The symbols B and D each preferably have 0 to 3 substituents. The symbol A preferably has 0 to 4 substituents.

For details of compounds represented by general formula (1) and methods of manufacture thereof, knowledge about lophine dimers is available, for example, as disclosed in the specification of U.S. Pat. No. 3,552,973, fourth column, line 22, to sixth column, line 3, the entire disclosure of which is incorporated herein by reference.

General Formula (2)

where $P^0$ represents hydrogen atom, halogen atom, or aryl group, and X represents halogen atom.

Examples of halogen atoms represented by $P^0$ and X include fluorine atom, chlorine atom, bromine atom, and iodine atom, preferably chlorine atom and bromine atom.

Examples of compounds represented by general formula (2) include carbon tetrachloride, carbon tetrabromide, p-nitrobenzotribromide, bromotrichloromethane, benzotrichloride, hexabromoethane, iodoform, 1,1,1-tribromo-2-methyl-2-propanol, 1,1,2,2-tetrabromoethane, 2,2,2-tribromoethanol, and 1,1,1-trichloro-2-methyl-2-propanol.

[Chem. 2]

General Formula (3)

where R represents a substituent, and x represents an integer of 0 to 5.

The symbol R represents a substituent. Examples of substituents include nitro group, halogen atom, $C_1$ to $C_3$ alkyl group, $C_1$ to $C_3$ haloalkyl group, acetyl groups, haloacetyl group, and $C_1$ to $C_3$ alkoxy group. If R is present at a plurality of positions, each R may be the same or different.

The symbol x represents an integer of 0 to 5, preferably 0 to 3.

Examples of compounds represented by general formula (3) include o-nitro-α,α,α-tribromoacetophenone, m-nitro-α,α,α-tribromoacetophenone, p-nitro-α,α,α-tribromoacetophenone, α,α,α-tribromoacetophenone, and α,α,α-tribromo-3,4-dichloroacetophenone.

General Formula (4)

where $R^1$ represents an optionally substituted alkyl group or an optionally substituted aryl group, and $X^1$ is halogen atom.

The symbol $R^1$ represents an optionally substituted alkyl group or an optionally substituted aryl group. Preferred examples of optionally substituted alkyl groups include alkyl groups having 1 to 20 carbon atoms, more preferably alkyl groups having 1 to 10 carbon atoms, even more preferably alkyl groups having 1 to 6 carbon atoms.

Preferred examples of optionally substituted aryl groups include aryl groups having 6 to 20 carbon atoms, more preferably aryl groups having 6 to 14 carbon atoms, even more preferably aryl groups having 6 to 10 carbon atoms.

Examples of substituents include nitro group, halogen atom, $C_1$ to $C_3$ alkyl group, $C_1$ to $C_3$ haloalkyl group, acetyl group, haloacetyl group, and $C_1$ to $C_3$ alkoxy group.

Examples of halogen atoms represented by $X^1$ include fluorine, chlorine, bromine, and iodine, preferably chlorine and bromine.

Examples of compounds represented by general formula (4) include 2,4-dinitrobenzenesulfonyl chloride, o-nitrobenzenesulfonyl chloride, m-nitrobenzenesulfonyl chloride, 3,3'-diphenylsulfonedisulfonyl chloride, ethanesulfonyl chloride, p-bromobenzenesulfonyl chloride, p-nitrobenzenesulfonyl chloride, p-3-benzenesulfonyl chloride, p-acetamidobenzenesulfonyl chloride, p-chlorobenzenesulfonyl chloride, p-toluenesulfonyl chloride, methanesulfonyl chloride, and benzenesulfonyl bromide.

General Formula (5)

where $R^2$ represents an optionally substituted alkyl group or an optionally substituted aryl group, and $X^2$ represents halogen atom.

The symbol $R^2$ represents an optionally substituted alkyl group or an optionally substituted aryl group as defined for $R^1$ in general formula (4), and preferred examples of alkyl and aryl groups are as listed above. Examples of halogen atoms represented by $X^2$ include fluorine, chlorine, bromine, and iodine, preferably chlorine and bromine.

Examples of compounds represented by general formula (5) include 2,4-dinitrobenzenesulfenyl chloride and o-nitrobenzenesulfenyl chloride.

[Chem. 3]

General Formula (6)

where $R^3$ represents an optionally substituted aryl group or an optionally substituted heteroaryl group; and $X^3$, $X^4$, and $X^5$ are each independently hydrogen atom or halogen atom, with the proviso that not all of $X^3$, $X^4$, and $X^5$ are hydrogen atom.

The symbol $R^3$ represents an optionally substituted aryl group or an optionally substituted heteroaryl group.

Preferred examples of aryl groups include aryl groups having 6 to 20 carbon atoms, more preferably aryl groups having 6 to 14 carbon atoms, even more preferably aryl groups having 6 to 10 carbon atoms.

Preferred examples of heteroaryl groups include heteroaryl groups having 4 to 20 carbon atoms, more preferably heteroaryl groups having 4 to 13 carbon atoms, even more preferably heteroaryl groups having 4 to 9 carbon atoms.

Examples of substituents include nitro group, halogen atom, $C_1$ to $C_3$ alkyl group, $C_1$ to $C_3$ haloalkyl group, acetyl group, haloacetyl atom, and $C_1$ to $C_3$ alkoxy group.

Examples of halogen atoms represented by $X^3$, $X^4$, and $X^5$ include fluorine, chlorine, bromine, and iodine, preferably chlorine and bromine.

Examples of compounds represented by general formula (6) include hexabromodimethyl sulfoxide, pentabromodimethyl sulfoxide, hexabromodimethylsulfone, trichloromethylphenylsulfone, tribromomethylphenylsulfone, trichloromethylphenylsulfone, trichloro-p-chlorophenylsulfone, tribromomethyl-p-nitrophenylsulfone, 2-trichloromethylbenzothiazolesulfone, 4,6-dimethylpyrimidine-2-tribromomethylsulfone, tetrabromodimethylsulfone, 2,4-dichlorophenyltrichloromethylsulfone, 2-methyl-4-chlorophenyltrichloromethylsulfone, 2,5-dimethyl-4-chlorophenyltrichloromethylsulfone, 2,4-dichlorophenyltrimethylsulfone, tribromomethylphenylsulfone, and tri-p-tolylsulfonium trifluoromethanesulfonate.

General Formula (7)

where $R^4$ represents an optionally substituted heteroaryl group; and $X^6$, $X^7$, and $X^8$ are each independently hydrogen atom or halogen atom, with the proviso that not all of $X^6$, $X^7$, and $X^8$ are hydrogen atom.

The symbol $R^4$ represents an optionally substituted heteroaryl group. Preferred examples of heteroaryl groups include heteroaryl groups having 4 to 20 carbon atoms, more preferably heteroaryl groups having 4 to 13 carbon atoms, even more preferably heteroaryl groups having 4 to 9 carbon atoms.

Examples of substituents include nitro group, halogen atom, $C_1$ to $C_3$ alkyl group, $C_1$ to $C_3$ haloalkyl group, acetyl group, haloacetyl atom, and $C_1$ to $C_3$ alkoxy group.

Examples of halogen atoms represented by $X^6$, $X^7$, and $X^8$ include fluorine, chlorine, bromine, and iodine, preferably chlorine and bromine.

Examples of compounds represented by general formula (7) include tribromoquinaldine, 2-tribromomethyl-4-methylquinoline, 4-tribromomethylpyrimidine, 4-phenyl-6-tribromomethylpyrimidine, 2-trichloromethyl-6-nitrobenzothiazole, 1-phenyl-3-trichloromethylpyrazole, 2,5-ditribromomethyl-3,4-dibromothiophene, 2-trichloromethyl-3-(p-butoxystyryl)-1,3,4-oxadiazole, 2,6-ditrichloromethyl-4-(p-methoxyphenyl)triazine, and 2-(4-methylphenyl)-4,6-bis(trichloromethyl)-1,3,5-triazine.

In particular, preferred are compounds represented by general formulae (3), (6), and (7), where the halogen atoms are preferably chlorine, bromine, or iodine. Compounds other than compounds represented by general formulae (1) to (7) can also be used, including diazo compounds such as bis(t-butylsulfonyl)diazomethane.

[Reductant]

The ultraviolet-sensing layer used in the present invention may contain a reductant. The reductant may be present inside or outside the capsules. The reductant functions to deactivate the photo-oxidant. The reductant prevents a rapid change in color density due to a rapid increase in the number of radicals generated from the photo-oxidant upon ultraviolet irradiation. This allows the color density to change continuously depending on the ultraviolet dose and thus allows the ultraviolet dose to be visually determined.

Such reductants may be used alone or in combination. Any reducing substance that functions to deactivate the photo-oxidant may be used.

The reductant used in the present invention may be any reductant that functions as a free-radical scavenger, i.e., a substance that traps free radicals generated from activated photo-oxidant. Examples of such reductants include organic reductants disclosed in the specification of U.S. Pat. No. 3,042,513 (e.g., hydroquinone, catechol, resorcinol, hydroxyhydroquinone, pyrrologlucinol, and aminophenols such as o-aminophenol and p-aminophenol) and cyclic phenylhydrazides disclosed in the specification of Japanese Examined Patent Application Publication No. 62-39726 (e.g., 1-phenylpyrazolidin-3-one (Phenidone A, formula (1) below), 1-phenyl-4-methylpyrazolidin-3-one (Phenidone B, formula (2) below), 1-phenyl-4,4-dimethylpyrazolidin-3-one (Dimezone, formula (3) below), 3-methyl-1-p-sulfophenyl)-2-pyrazolin-5-one, and 3-methyl-1-phenyl-2-pyrazolin-5-one). Examples of commercially available reductants include 4-hydroxymethyl-4-methyl-1-phenyl-3-pyrazolidinone (Dimezone S, Daito Chemical Co., Ltd.).

[Chem. 4]

(1)

(2)

(3)

The cyclic phenylhydrazides may be substituted on the phenyl group. Examples of substituents include methyl group, trifluoromethyl group, chlorine atom, bromine atom, fluorine atom, methoxy group, ethoxy group, p-benzyloxy group, butoxy group, p-phenoxy group, 2,4,6-trimethyl group, and 3,4-dimethyl group.

The cyclic phenylhydrazides may be substituted on position 4 of the heterocyclic group. Examples of substituents include bis-hydroxymethyl group, hydroxymethyl group, methyl group, ethyl group, and benzyl group. The cyclic phenylhydrazides may be substituted on position 5 of the heterocyclic group. Examples of substituents include methyl and phenyl.

Other reductants may also be used, including guanidines, alkylenediamines, and hydroxyamines.

Examples of guanidines include phenylguanidine, 1,3-diphenylguanidine, 1,2,3-triphenylguanidine, 1,2-dicyclohexylguanidine, 1,2,3-tricyclohexylguanidine, 1,3-di-o-tolylguanidine, o-tolyldiphenylguanidine, m-tolyldiphenylguanidine, p-tolyldiphenylguanidine, N,N'-dicyclohexyl-4-morpholinocarboxyamidine, 1,3-ditolyl-3-phenylguanidine, 1,2-dicyclohexylphenylguanidine, 1-o-tolylbiguanide, and N-benzylidene-guanidinoamine.

Examples of alkylenediamines include ethylenediamine, propylenediamine, tetramethylenediamine, hexamethylenediamine, octamethylenediamine, 1,1,2-diaminododecane, and tetrabenzylethylenediamine.

Examples of hydroxyamines include diethanolamine, triethanolamine, and 3-β-naphthyloxy-1-N,N-dimethylamino-2-propanol.

The reductant used for the sheet according to the present invention may be dispersed in the form of solids, for example, in a sand mill, or may be dissolved and emulsified in oil.

The reductant may be dispersed in the form of solids in a solution of a water-soluble polymer with a concentration of 2% to 30% by mass. The dispersed particles preferably have a particle size of 10 μm or less. Preferred examples of water-soluble polymers include those used for the preparation of capsules. The reductant can be emulsified using the techniques and materials disclosed in Japanese Unexamined Patent Application Publication No. 63-045084.

If the reductant is present outside the capsules, the molar ratio of the photo-oxidant to the reductant is preferably 1:0.1 to 100, more preferably 1:0.5 to 0.50, even more preferably 1:1 to 10.

If the reductant is present inside the capsules, the molar ratio of the photo-oxidant to the reductant is preferably 1:0.001 to 0.1, more preferably 1:0.005 to 0.08, even more preferably 1:0.01 to 0.05.

<<Formation of Ultraviolet-Sensing Layer>>

The ultraviolet-sensing layer can be formed by coating or impregnating a support or reflective layer with a dispersion of capsules containing the leuco dye and the photo-oxidant described above or by forming a self-supported layer from the capsule dispersion.

The amount of ultraviolet-sensing layer coating composition applied to form the ultraviolet-sensing layer is preferably 3 to 30 g/m$^2$, more preferably 5 to 20 g/m$^2$, on a solid basis. If the amount of coating composition applied falls below 3 g/m$^2$, the resulting coating has an insufficient concentration. If the amount of coating composition applied exceeds 30 g/m$^2$, the resulting coating has no higher quality and is disadvantageous in terms of cost.

The ultraviolet-sensing layer coating composition can be applied by commonly known coating processes such as dip coating, air knife coating, curtain coating, roller coating, doctor coating, wire bar coating, slide coating, gravure coating, spin coating, and extrusion coating using hoppers, as disclosed in the specification of U.S. Pat. No. 2,681,294.

<<<Support>>>

Any support may be used in the present invention without departing from the spirit of the present invention.

Examples of materials suitable for the support include materials commonly used in graphic art and decoration, including paper; films of plastics and polymers, such as regenerated cellulose, cellulose acetate, cellulose nitrate, poly(ethylene terephthalate), vinyl polymers and copolymers, polyethylene, polyvinyl acetate, poly(methyl methacrylate), and poly(vinyl chloride); woven fabric; glass; wood; and metals.

The support preferably has a thickness of 5 to 250 μm, more preferably 25 to 150 μm, even more preferably 50 to 100 μm.

<<<Reflective Layer>>>

The ultraviolet-sensing sheet according to the present invention may include a reflective layer between the support and the ultraviolet-sensing layer or on a surface of the support, the surface being away from the ultraviolet-sensing layer. The reflective layer can be provided to improve the reflection density. The reflective layer is not necessary if the support itself is reflective; if the support is transparent, the reflective layer is preferably provided to reduce light transmission.

The reflective layer used in the present invention is preferably formed by coating on one surface of the support and preferably contains a binder and white inorganic particles. The white inorganic particles are preferably present in the reflective layer in an amount of 30% to 90% of the total mass of the binder and the white inorganic particles in the reflective layer.

The reflective layer may further contain other optional components, such as various additives.

[White Inorganic Particles]

The reflective layer used in the present invention preferably contains at least one type of white inorganic particles. The white inorganic pigment may be the same as or different from the white inorganic particles present in the polymer substrate. For example, inorganic pigments, such as titanium dioxide, barium sulfate, silicon oxide, aluminum oxide, magnesium oxide, calcium carbonate, kaolin, and talc, may be selected. In particular, titanium dioxide is preferred. Examples of commercially available inorganic pigments include the TIPAQUE series, such as TIPAQUE R780-2 (Ishihara Sangyo Kaisha, Ltd.).

The white, inorganic particles are preferably present in the reflective layer used in the present invention in an amount of 30% to 90% by mass, more preferably 50% to 85% by mass, of the total mass of the binders and the white inorganic particles in the reflective layer. If the white inorganic particles are present in an amount of less than 30% by mass, the reflective layer has low reflectance. If the white inorganic particles are present in an amount of more than 90% by mass, the weight of the reflective layer cannot be reduced.

The white inorganic particles are preferably present in the reflective layer used in the present invention in an amount of 4 to g/m$^2$, more preferably 5 to 11 g/m$^2$. If the white inorganic particles are present in an amount of 4 g/m$^2$ or more, the necessary reflectance can be readily achieved. If the white inorganic particles are present in an amount of 12 g/m$^2$ or less, the weight of the sheet according to the present invention can be readily reduced.

If the reflective layer contains two or more types of white inorganic particles, the total amount of white inorganic particles present in the reflective layer must be 4 to 12 g/m$^2$.

The white inorganic particles preferably have an average particle size of 0.1 to 10 μm, more preferably about 0.3 to about 8 μm, in terms of volume average particle size. White inorganic particles having such average particle sizes have high light reflectivity. The average particle size is measured with an LA950 laser scattering particle size distribution analyzer (HORIBA, Ltd.).

[Binder]

The reflective layer used in the present invention preferably contains at least one binder. The binder is preferably present in an amount of 0.5 to 5.0 g/m$^2$, more preferably 1 to 3 g/m$^2$. If the binder is present in an amount of 0.5 g/m$^2$ or more, the reflective layer has sufficient strength. If the binder is present in an amount of 5 g/m$^2$ or less, the reflective layer has suitable reflectance and mass.

Examples of binders suitable for the reflective layer used in the present invention include poly(vinyl alcohol) (PVA), modified poly(vinyl alcohol)s, hydroxyethyl cellulose, hydroxypropyl cellulose, epichlorohydrin-modified polyamides, ethylene-maleic anhydride copolymers, styrene-maleic anhydride copolymers, isobutylene-maleic anhydride-salicylic acid copolymers, polyacrylic acid, polyacrylamide, methylol-modified polyacrylamides, starch derivatives, casein, gelatin, and styrene-butadiene rubber (SBR). To impart water resistance to these binders, water resistance improvers and hydrophobic polymer emulsions such as acrylic resin emulsions and styrene-butadiene latex may be added. To provide high transparency, poly(vinyl alcohol) is preferably used, and modified PVAs such as carboxy-modified poly(vinyl alcohol)s and alkyl ether-modified poly(vinyl alcohol)s can also be used.

[Additives]

The reflective layer used in the present invention may optionally contain components other than binders and white inorganic particles. Any other component may be selected depending on the purpose and need. Examples of other components include crosslinking agents, surfactants, and fillers.

The crosslinking agent may be selected from known crosslinking agents. Examples of crosslinking agents include water-soluble initial condensates, such as N-methylolurea, N-methylolmelamine, and urea-formalin; dialdehydes, such as glyoxal and glutaraldehyde; inorganic crosslinking agents, such as boric acid and borax; and polyamide-epichlorohydrin.

If a water-soluble polymer (e.g., gelatin or poly(vinyl alcohol)) is used as the binder, it can be crosslinked with the crosslinking agent to further improve the storage stability.

The crosslinking agent, when used, is preferably present in an amount of 5% to 50% by mass, more preferably 10% to 40% by mass, of the binder in the reflective layer. If the crosslinking agent is present in an amount of 5% by mass or more, it has a sufficient crosslinking effect while maintaining the strength and adhesion of the reflective layer. If the crosslinking agent is present in an amount of 50% by mass or less, the coating composition has a prolonged pot life.

The surfactant may be selected from known surfactants such as anionic surfactants and nonionic surfactants. The surfactant, when used, is preferably present in an amount of 0.1 to 15 $mg/m^2$, more preferably 0.5 to 5 $mg/m^2$. If the surfactant is present in an amount of 0.1 $mg/m^2$ or more, a smooth layer can be formed without repellency. If the surfactant is present in an amount of 15 $mg/m^2$ or less, the reflective layer has high adhesion.

The reflective layer used in the present invention may contain fillers such as silica in addition to the white inorganic particles. The filler, when used, is preferably present in an amount of 20% by mass or less, more preferably 15% by mass or less, of the binder in the reflective layer. If the filler is present in an amount of 20% by mass or less, the reflective layer has the necessary reflectance and adhesion to the support.

<<Formation of Reflective Layer>>

The reflective layer used in the present invention is formed on at least one surface of the support by applying a reflective layer coating composition containing white inorganic particles, a binder, and other additives.

The coating composition can be applied by known coating processes such as gravure coating and bar coating.

The coating composition may be a water-based coating composition containing water as a coating solvent or may be a solvent-based coating composition containing an organic solvent such as toluene or methyl ethyl ketone. In particular, a preferred solvent is water, which is environmentally friendly. Such coating solvents may be used alone or in mixture. Preferred examples of the coating solvents include water and a mixture of water and methyl alcohol in a mass ratio of 95:5.

The reflective layer coating composition may be applied to the surface of the polymer substrate directly or with a primer layer having a thickness of 2 μm or less therebetween to form the reflective layer on the polymer substrate.

The reflective layer coating composition is preferably applied in an amount of 5 $g/m^2$ or more, more preferably 10 $g/m^2$ or more, on a solid basis. The reflective layer coating composition should be applied in an amount of 30 $g/m^2$ or less, although no critical upper limit is defined. If the reflective layer coating composition is applied in an amount of less than 5 $g/m^2$, the reflective layer has insufficient reflection density.

The reflective layer preferably has a thickness of 5 to 30 μm, more preferably 7 to 20 μm, even more preferably 9 to 15 μm.

<<Adhesion Layer>>

The ultraviolet-sensing sheet according to the present invention may include an adhesion layer between the support and the reflective layer. The adhesion layer preferably contains a binder, a crosslinking agent, and a surfactant.

The binder may be similar to the binder used to form the reflective layer, preferably a styrene-butadiene rubber (SBR) binder.

The crosslinking agent may be similar to the crosslinking agent used to form the reflective layer, preferably glyoxal.

The surfactant may be similar to the surfactant used to form the reflective layer, preferably an anionic surfactant, more preferably a sodium alkylbenzenesulfonate.

<<Formation of Adhesion Layer>>

The adhesion layer used in the present invention is formed by applying an adhesion layer coating composition containing components such as binders to a surface of the support. The method for applying the adhesion layer coating composition and the preferred amount of adhesion layer coating composition applied may be similar to those for the reflective layer.

<<Glossy Layer>>

The glossy layer used in the present invention is preferably formed on at least one surface of the reflective layer and preferably contains a binder and a pigment. The pigment is preferably present in the glossy layer in an amount of 30% to 90% of the total mass of the binder and the pigment in the glossy layer.

The type and preferred amount of binder used may be similar to those for the reflective layer.

The glossy layer may optionally contain other components, such as various additives. The types and preferred amounts of additives used may be similar to those for the reflective layer.

[Pigment]

Examples of pigments include both organic pigments and inorganic pigments. Examples of the organic pigments include monoazo pigments, condensed azo pigments, anthraquinone pigments, isoindolinone pigments, heterocyclic pigments, perinone pigments, quinacridone pigments, perylene pigments, thioindigo pigments, and dioxazine pigments. Examples of the inorganic pigments include carbon blacks, titanium oxide, titanium yellow, iron oxides, ultramarine, cobalt blue, baked pigments, and metallic pigments.

Preferred examples of the carbon blacks include channel black, furnace black, lamp black, thermal black, Ketjen black, and naphthalene black. These carbon blacks may be used alone or in combination with each other or with other colorants. Examples of the metallic pigments include metal particles, such as aluminum, colored aluminum, nickel, tin, copper, gold, silver, platinum, iron oxide, stainless steel, and titanium particles; mica pearl pigments; colored graphite; colored glass fibers; colored glass flakes; and pearl pigments.

Commercially available pigments such as Iriodin 111 (Merck) can also be used.

<<Formation of Glossy Layer>>

The glossy layer used in the present invention is formed by applying a glossy layer coating composition containing a pigment, a binder, and other additives to the surface of the reflective layer. The method for applying the glossy layer coating composition and the preferred amount of glossy layer coating composition applied may be similar to those for the reflective layer.

The glossy layer preferably has a thickness of 0.5 to 20 μm, more preferably 0.7 to 15 μm, even more preferably 1 to 5 μm.

<Method for Sensing Ultraviolet>

The ultraviolet-sensing sheet according to the present invention makes possible to continuously develop color depending on the cumulative illuminance and thus allows the ultraviolet dose to be visually determined and detected. In particular, the ultraviolet-sensing sheet is suitable in determination of ultraviolet doses in a range from 1 to 1,000 $mJ/cm^2$ and can thus be widely used in a method for detecting ultraviolet and a method for measuring ultraviolet.

By the ultraviolet-sensing sheet of the present invention is a sheet form, the ultraviolet-sensing sheet can also measure the ultraviolet irradiance over a wide area.

The ultraviolet-sensing sheet according to the present invention, since a sheet form, can be simply placed on a site where measurement ultraviolet radiation is intended to measure ultraviolet radiation.

<Application of Ultraviolet-Sensing Sheet>

The ultraviolet-sensing sheet according to the present invention, which allows the ultraviolet dose to be visually determined, facilitates ultraviolet illuminance over a wide area, and particularly, is effective in determination of ultraviolet doses in a range from 1 to 1,000 mJ/cm$^2$, can be used in various applications. For example, when a film is manufactured in a roll-to-roll process by curing an ultraviolet-curable resin with ultraviolet radiation from an ultraviolet irradiation system, the ultraviolet-sensing sheet can be used to measure the ultraviolet dose of the ultraviolet-curable resin without using an ultraviolet dosimeter. The ultraviolet-sensing sheet can also be used for routine measurement of ultraviolet dose during daytime, for example, to access sun damage to human skin and other objects.

EXAMPLES

The present invention is further illustrated by the following examples. The following specific examples should not be construed as limiting the scope of the present invention; various modifications may be made to the conditions illustrated in the following examples, including the types, amounts, and ratios of materials used and the types and sequences of processes, without departing from the spirit of the present invention. The term "part(s)", indicating the amount of material added, means part(s) by mass.

(Preparation of Ultraviolet-Sensing Sheet)

Example 1

A mixture having the following composition was added to an aqueous solution containing 63 parts of 8 mass % aqueous poly(vinyl alcohol) solution and 100 parts of distilled water. The mixture was emulsified at 20° C. to give an emulsion having a volume average particle size of 1 μm. The resulting emulsion was stirred at 40° C. for 3 hours. The emulsion was then cooled to room temperature and was filtered to give an aqueous capsule dispersion.

—Composition of Mixture—

| | |
|---|---|
| Leuco dye: leuco crystal violet (LCV, Yamada Chemical Co., Ltd.) | 3.0 parts |
| Photo-oxidant: tribromomethylphenylsulfone (BMPS) | 1.5 parts |
| Methylene chloride | 22 parts |
| Tricresyl phosphate | 24 parts |
| TAKENATE D-110N (75 mass % solution in ethyl acetate, Mitsui Chemicals, Inc.) | 24 parts |

A mixture having the following composition was then dispersed in a DYNO-MILL (Willy A. Bachofen AG) to give a dispersion of 4-hydroxymethyl-4-methyl-1-phenyl-3-pyrazolidinone (Dimezone S) having an average particle size of 3 μm.

Composition of Mixture

| | |
|---|---|
| 4 mass % aqueous poly(vinyl alcohol) solution | 150 parts |
| Reductant: 4-hydroxymethyl-4-methyl-1-phenyl-3-pyrazolidinone (Dimezone S, Daito Chemical Co., Ltd.) | 30 parts |

A mixture was prepared from 9 parts of the resulting capsule dispersion and 9 parts of the resulting Dimezone S dispersion, was applied to a foamed poly(ethylene terephthalate) base having a thickness of 75 μm (Crisper K1212, Toyobo Co., Ltd.) in an amount of 10 g/m$^2$ on a solid basis, and was dried by heating at 50° C. for 1 minute to prepare an ultraviolet-sensing sheet of Example 1.

Example 2

An ultraviolet-sensing sheet was prepared as in Example 1 except that the amount of photo-oxidant was changed from 1.5 parts in Example 1 to 0.9 part.

Example 3

An ultraviolet-sensing sheet was prepared as in Example 1 except that the amount of photo-oxidant was changed from 1.5 parts in Example 1 to 2.4 parts.

Example 4

An ultraviolet-sensing sheet was prepared as in Example 1 except that the amount of photo-oxidant was changed from 1.5 parts in Example 1 to 0.75 part, and the amount of leuco dye was changed from 3.0 parts in Example 1 to 1.5 parts.

Example 5

An ultraviolet-sensing sheet was prepared as in Example 1 except that the amount of photo-oxidant was changed from 1.5 parts in Example 1 to 3.5 parts, and the amount of leuco dye was changed from 3.0 parts in Example 1 to 7.0 parts.

Example 6

An ultraviolet-sensing sheet was prepared as in Example 1 except that the photo-oxidant in Example 1 was replaced with tri-p-tolylsulfonium trifluoromethanesulfonate (TS-01, Sanwa Chemical Co., Ltd.).

Example 7

An ultraviolet-sensing sheet was prepared as in Example 1 except that the photo-oxidant in Example 1 was replaced with bis(t-butylsulfonyl)diazomethane (WPAG-170, Wako Pure Chemical Industries, Ltd.).

Example 8

An ultraviolet-sensing sheet was prepared as in Example 1 except that the photo-oxidant used in Example 1 was replaced with lophine dimer (B-CIM, Hodogaya Chemical Co., Ltd.).

Comparative Example 1

An ultraviolet-sensing sheet was prepared as in Example 1 except that the amount of photo-oxidant was changed from 1.5 parts in Example 1 to 0.3 part.

Comparative Example 2

An ultraviolet-sensing sheet was prepared as in Example 1 except that the amount of photo-oxidant was changed from 1.5 parts in Example 1 to 4.5 parts.

Comparative Example 3

An ultraviolet-sensing sheet was prepared as in Example 1 except that the amount of photo-oxidant was changed from 1.5 parts in Example 1 to 0.25 part, and the amount of leuco dye was changed from 3.0 parts in Example 1 to 0.5 part.

Comparative Example 4

An ultraviolet-sensing sheet was prepared as in Example 1 except that the amount of photo-oxidant was changed from 1.5 parts in Example 1 to 0.65 part, and the amount of leuco dye was changed from 3.0 parts in Example 1 to 13 parts.

Comparative Example 5

An ultraviolet-sensing sheet was prepared as in Example 1 except that the tribromomethylphenylsulfone (BMPS) used as a photo-oxidant in Example 1 was replaced with 2-(4-methylphenyl)-4,6-bis(trichloromethyl)-1,3,5-triazine (Triazin A, Siber Hegner & Co.).

Comparative Example 6

An ultraviolet-sensing sheet was prepared as in Example 1 except that the leuco dye or the photo-oxidant was not encapsulated in the ultraviolet-sensing layer in Example 1.

[Measurement of ε (Photosensitive Region) of Photo-Oxidant]

The ε values (molar absorption coefficients) at wavelengths of 250 and 350 nm were measured with a spectrophotometer (U-2000, Hitachi High-Technologies Corporation).

[Evaluations]

The resulting ultraviolet-sensing sheets of the Examples and the Comparative Examples were tested and evaluated for their changes in reflection density ΔD after coloration, ease of handling, and image stability as follows. The results are summarized in the table below.

[Change in Reflection Density]

The ultraviolet-sensing sheets were irradiated with ultraviolet radiation from a high-pressure mercury lamp (high-pressure ultraviolet lamp, Ushio Inc.) to cumulative illuminance of 1 mJ/cm$^2$, 10 mJ/cm$^2$, 100 mJ/cm$^2$, and 1,000 mJ/cm$^2$. The change in color density after the irradiation was determined by measuring the change in color after the irradiation with a reflection densitometer (X-Rite 310, X-Rite Inc.). Specifically, the change in reflection density ΔD1 in a range of 1 mJ/cm$^2$ or more and less than 10 mJ/cm$^2$, the change in reflection density ΔD2 in a range of 10 mJ/cm$^2$ or more and less than 100 mJ/cm$^2$, and the change in reflection density ΔD3 in a range of 100 mJ/cm$^2$ or more and 1,000 mJ/cm$^2$ or less, were determined and evaluated according to the following criteria:

A: all of the changes in reflection density ΔD1, ΔD2, and ΔD3 are 0.2 or more.

B: at least one of the changes in reflection density ΔD1, ΔD2, and ΔD3 is less than 0.2.

The measurements, which are assumed to give an ascending curve as shown in FIG. 1, were taken at the upper and lower limits of each range of cumulative illuminance; therefore, the values of ΔD1, ΔD2, and ΔD3 are synonymous with the difference between the maximum and minimum values. As ΔD1, ΔD2, and ΔD3 increase, the measurable range can be expanded, and thus, superior gradation can be achieved.

[Ease of Handling]

The ultraviolet-sensing sheets were left standing under a fluorescent lamp with an illuminance of 500 lux for 30 minutes. The changes in the densities of the ultraviolet-sensing sheets after 30 minutes were measured with a reflection densitometer (X-Rite 310, X-Rite Inc.) and were evaluated according to the following criteria:

A: 0.1 or less
B: more than 0.1 and 0.3 or less
C: more than 0.3

[Image Stability]

The ultraviolet-sensing sheets were irradiated with an ultraviolet radiation from a high-pressure mercury lamp (high-pressure ultraviolet lamp, Ushio Inc.) to an ultraviolet dose of 100 mJ/cm$^2$ and were treated in a dry oven at 100° C. for 3 minutes. The ultraviolet-sensing sheets were then irradiated again with an ultraviolet radiation from the high-pressure mercury lamp to an ultraviolet dose of 100 mJ/cm$^2$. The change in density after the irradiation was measured with a reflection densitometer (X-Rite 310, X-Rite Inc.) and was evaluated according to the following criteria:

A: 0.1 or less
B: more than 0.1 and 0.2 or less
C: more than 0.2

TABLE 1

| | | Example 1 | Example 2 | Example 3 | Example 4 | Example 5 | Example 6 | Example 7 | Example 8 |
|---|---|---|---|---|---|---|---|---|---|
| Ultraviolet-Sensing Layer | Photo-oxidants | BMPS | BMPS | BMPS | BMPS | BMPS | TS-01 | WPAG-170 | B-CIM |
| | Photo-oxidants/Leuco dyes (mass rate) | 0.5 | 0.3 | 0.8 | 0.5 | 0.5 | 0.5 | 0.5 | 0.5 |
| | The amounts of Leuco dyes per surface area of 1 m$^2$ of the ultraviolet-Sensing Layer | 0.3 | 0.3 | 0.3 | 0.15 | 0.7 | 0.3 | 0.3 | 0.3 |
| | ε (350 nm) | 280 | 280 | 280 | 280 | 280 | 320 | 650 | 3290 |
| | ε (250 nm) | 12730 | 12730 | 12730 | 12730 | 12730 | 12630 | 12690 | 12740 |
| | The presence or absence of capsules | presence | presence | presence | presence | presence | presence | presence | presence |
| Evaluations | Change in reflection density ΔD1 (1-10 mJ/cm$^2$) | 0.23 | 0.21 | 0.35 | 0.22 | 0.36 | 0.25 | 0.27 | 0.37 |
| | Change in reflection density ΔD2 (10-100 mJ/cm$^2$) | 0.27 | 0.25 | 0.28 | 0.24 | 0.25 | 0.28 | 0.29 | 0.22 |
| | Change in reflection density ΔD3 (100-1000 mJ/cm$^2$) | 0.29 | 0.24 | 0.22 | 0.23 | 0.21 | 0.28 | 0.28 | 0.21 |
| | Change in Reflection Density | A | A | A | A | A | A | A | A |
| | Ease of Handling | A | A | A | A | A | A | A | B |
| | Image Stability | A | A | A | A | A | A | A | A |

TABLE 2

|  |  | Comparative Example 1 | Comparative Example 2 | Comparative Example 3 | Comparative Example 4 | Comparative Example 5 | Comparative Example 6 |
|---|---|---|---|---|---|---|---|
| Ultraviolet-Sensing Layer | Photo-oxidants | BMPS | BMPS | BMPS | BMPS | Triazin A | BMPS |
|  | Photo-oxidants/Leuco dyes (mass rate) | 0.1 | 1.5 | 0 | 0.5 | 0.5 | 0.5 |
|  | The amounts of Leuco dyes per surface area of 1 $m^2$ of the ultraviolet-Sensing Layer | 0.3 | 0.3 | 0.05 | 1.3 | 0.3 | 0.3 |
|  | $\epsilon$ (350 nm) | 280 | 280 | 280 | 280 | 11760 | 280 |
|  | $\epsilon$ (250 nm) | 12730 | 12730 | 12730 | 12730 | 10380 | 12730 |
|  | The presence or absence of capsules | presence | presence | presence | presence | presence | absence |
| Evaluations | Change in reflection density $\Delta D1$ (1-10 mJ/$cm^2$) | 0.13 | 0.45 | 0.10 | 0.42 | 0.51 | 0.02 |
|  | Change in reflection density $\Delta D2$ (10-100 mJ/$cm^2$) | 0.11 | 0.12 | 0.09 | 0.38 | 0.15 | 0.03 |
|  | Change in reflection density $\Delta D3$ (100-1000 mJ/$cm^2$) | 0.10 | 0.05 | 0.09 | 0.11 | 0.05 | 0.02 |
|  | Change in Reflection Density | B | B | B | B | B | B |
|  | Ease of Handling | A | A | A | A | C | A |
|  | Image Stability | A | A | A | A | A | C |

As shown in the tables, in Examples 1 to 8, all of the change in reflection density $\Delta D1$ of 0.2 or more in a range of cumulative illuminance of 1 mJ/$cm^2$ or more and less than 10 mJ/$cm^2$, the change in reflection density $\Delta D2$ of 0.2 or more in a range of cumulative illuminance of 10 mJ/$cm^2$ or more and less than 100 mJ/$cm^2$, and the change in reflection density $\Delta D3$ of 0.2 or more in a range of cumulative illuminance of 100 mJ/$cm^2$ or more and 1,000 mJ/$cm^2$, and the change in reflection density was evaluated as rank A, which indicates superior gradation.

In contrast, in Comparative Examples 1 to 6, at least one of the change in reflection density $\Delta D1$ in a range of cumulative illuminance of 1 mJ/$cm^2$ or more and less than 10 mJ/$cm^2$, the change in reflection density $\Delta D2$ in a range of cumulative illuminance of 10 mJ/$cm^2$ or more and less than 100 mJ/$cm^2$, and the change in reflection density $\Delta D3$ in a range of cumulative illuminance of 100 mJ/$cm^2$ or more and less than or equal to 1,000 mJ/$cm^2$ was less than 0.2, which indicates poor gradation.

The results also indicate that the ultraviolet-sensing sheets of Examples 1 to 7, which contained photo-oxidants having molar absorption coefficients E of 2,000 or less at a wavelength of 350 nm and 10,000 or more at a wavelength of 250 nm, had greater ease of handling.

The results also indicate that the ultraviolet-sensing sheets including an ultraviolet-sensing layer containing capsules and a reductant had high image stability.

These results demonstrate that the ultraviolet-sensing sheet according to the present invention is effective in ultraviolet dosimetry in the range from 1 to 1,000 mJ/$cm^2$.

Example 9

An ultraviolet-sensing sheet of Example 9 was prepared by forming an ultraviolet-sensing layer as in Example 1 on a reflective layer formed as follows.
<Formation of Reflective Layer>
A mixture having the following composition was dispersed in a DYNO-MILL (Willy A. Bachofen AG) to give a dispersion of titanium oxide particles having an average particle size of 1 μm.
—-Composition of Mixture—

| 4 mass % aqueous poly(vinyl alcohol) solution | 80 parts |
|---|---|
| Titanium oxide (TIPAQUE R780-2, Ishihara Sangyo Kaisha, Ltd.) | 50 parts |

A mixture was prepared from 10 parts of the resulting titanium oxide dispersion and 20 parts of 6 mass % aqueous poly(vinyl alcohol) solution, was applied to a poly(ethylene terephthalate) base in an amount of 10 g/$m^2$ on a solid basis, and was dried at 80° C. for 1 minute to form a reflective layer.

Example 10

An ultraviolet-sensing sheet was prepared as in Example 9 except that the titanium oxide particles having a particle size of 1 μm in Example 9 were replaced with titanium oxide particles having a particle size of 0.3 μm.

Example 11

An ultraviolet-sensing sheet was prepared as in Example 9 except that the titanium oxide particles having a particle size of 1 μm in Example 9 were replaced with titanium oxide particles having a particle size of 8 μm.

Example 12

An ultraviolet-sensing sheet was prepared as in Example 9 except that the titanium oxide particles having a particle size of 1 μm in Example 9 were replaced with titanium oxide particles having a particle size of 1 μm, and the mixture was applied in an amount of 6 g/$m^2$ on a solid basis.

Example 13

An adhesion layer was formed on a poly(ethylene terephthalate) base as follows.
<Formation of Adhesion Layer>
A mixture having the following composition was prepared as an adhesion layer coating composition.
—Composition of Mixture—

| 4 weight % aqueous poly(vinyl alcohol) solution | 98 parts |
|---|---|
| SBR binder solution (SN-307, Nippon A&L Inc.) | 1,877 parts |
| Crosslinking agent (glyoxal, Nippon Synthetic Chemical Industry Co., Ltd.) | 18 parts |
| ABS surfactant (Neogen T, Daiichi Kagaku Kogyo Co., Ltd.) | 6 parts |

The resulting adhesion layer coating composition was applied to a poly(ethylene terephthalate) base in an amount of 2.0 g/m² on a solid basis and was dried at 80° C. for 1 minute to form an adhesion layer.

A reflective layer was formed on the surface of the adhesion layer as in Example 9. An ultraviolet-sensing layer was then formed on the surface, away from the reflective layer, of the poly(ethylene terephthalate) base as in Example 1 to prepare an ultraviolet-sensing sheet of Example 13.

Example 14

An ultraviolet-sensing sheet of Example 14 was prepared as in Example 13 except that a glossy layer was formed on the reflective layer in Example 13 as follows.
<Formation of Glossy Layer>
A mixture having the following composition was dispersed in a DYNO-MILL (Willy A. Bachofen AG) to give a dispersion of a pearl pigment having an average particle size of 5 μm.
—Composition of Mixture—

| | |
|---|---|
| 4 weight % aqueous poly(vinyl alcohol) solution | 80 parts |
| Pearl pigment (Iriodin 111, Merck) | 50 parts |

A mixture was prepared from 10 parts of the resulting pearl pigment dispersion and 20 parts of 6 mass % aqueous poly(vinyl alcohol) solution, was applied to the reflective layer in an amount of 1.0 g/m² on a solid basis, and was dried at 80° C. for 1 minute to form a glossy layer.

Example 15

An ultraviolet-sensing sheet was prepared as in Example 14 except that the glossy layer in Example 14 was formed by applying the coating composition in an amount of 3.0 g/m² on a solid basis.

(Evaluations)

The resulting ultraviolet-sensing sheets of Examples 9 to 15 were tested and evaluated for reflection density as follows. The results are summarized in the table below.
[Reflection Density]
The ultraviolet-sensing sheets were irradiated with ultraviolet radiation from a high-pressure mercury lamp (high-pressure ultraviolet lamp, Ushio Inc.) to a cumulative illuminance of 100 mJ/cm². The change in color after the irradiation was measured with a reflection densitometer (X-Rite 310, X-Rite Inc.) and was evaluated according to the following criteria:
A: more than 0.5
B: more than 0.4 and 0.5 or less
C: 0.4 or less
[Evaluation of Curling]
A4-sized samples were left standing at 15° C. and 30% for one day, with the photosensitive surface (ultraviolet-sensing layer) thereof facing upward. The heights (mm) of rising at the four corners were measured and averaged.
[Distinguishability between Front and Back Surfaces]
The gloss at 60° was measured with a digital variable-angle gloss meter (UGV-6P, Suga Test Instruments Co., Ltd.). The color difference was measured with a spectrocolorimeter (CM-3700A, Konica Minolta, Inc.).
A: a difference in gloss between front and back surfaces is 5 or more, or a color difference between front and back surfaces is 3 or more
B: a difference in gloss between front and back surfaces is 2 or more and less than 5, or a color difference between front and back surfaces is 1 or more and less than 3
C: a difference in gloss between front and back surfaces is less than 2, or a color difference between front and back surfaces is less than 1

TABLE 3

| | | Example 9 | Example 10 | Example 11 | Example 12 | Example 13 | Example 14 | Example 15 |
|---|---|---|---|---|---|---|---|---|
| Ultraviolet-Sensing Layer | Photo-oxidants | BMPS | BMPS | BMPS | BMPS | BMPS | BMPS | BMPS |
| | Photo-oxidants/Leuco dyes (mass rate) | 0.5 | 0.5 | 0.5 | 0.5 | 0.5 | 0.5 | 0.5 |
| | The amounts of Leuco dyes per surface area of 1 m² of the ultraviolet-Sensing Layer | 0.3 | 0.3 | 0.3 | 0.3 | 0.3 | 0.3 | 0.3 |
| | ε (350 nm) | 280 | 280 | 280 | 280 | 280 | 280 | 280 |
| | ε (250 nm) | 12730 | 12730 | 12730 | 12730 | 12730 | 12730 | 12730 |
| | The presence or absence of capsules | presence | presence | presence | presence | presence | presence | presence |
| Reflective Layer | The presence or absence of a reflective Layer | presence | presence | presence | presence | presence | presence | presence |
| | The particle size of the metal particles (μm) | 1 | 0.3 | 8 | 1 | 1 | 1 | 1 |
| | The coating amount for the Reflective Layer (g/m²) | 10 | 10 | 10 | 6 | 10 | 10 | 10 |
| | Placement point (Placement point in drawing) | FIG. 4 | FIG. 4 | FIG. 4 | FIG. 5 | FIG. 5 | FIG. 5 | FIG. 5 |
| Glossy Layer | The coating amount for the Glossy Layer (g/m²) | — | — | — | — | — | 1 | 3 |
| Evaluations | Reflection Density | A | A | A | A | A | A | A |
| | Curling (mm) | 20 | 20 | 20 | 16 | 0 | 0 | 0 |
| | Distinguishability between Front and Back Surfaces | A | A | A | A | B | A | A |

As shown in the table, the ultraviolet-sensing sheet according to the present invention has high reflection density if it includes a reflective layer formed on a transparent support.

The ultraviolet-sensing sheets of Examples 13 to 15, which have the structure shown in FIG. 5, exhibited little or no curling at low humidity. The ultraviolet-sensing sheets of Examples 14 and 15, which have the structure shown in FIG. 5 and include a glossy layer on the reflective layer, had high distinguishability between the front and back surfaces thereof.

Ultraviolet-sensing sheets prepared as in Examples 13 to 15 except that no reductant was used in the ultraviolet-sensing layer had superior properties as in Examples 13 to 15.

REFERENCE SIGNS LIST 1 ultraviolet-sensing sheet
10 ultraviolet-sensing layer
11 capsule
12 photo-oxidant
12a activated photo-oxidant
13 leuco dye
20 reflective layer
30 support
40 glossy layer
50 adhesion layer

What is claimed is:

1. An ultraviolet-sensing sheet which has a change in reflection density ΔD1 of 0.2 or more in a range of cumulative illuminance of 1 mJ/cm$^2$ or more and less than 10 mJ/cm$^2$, a change in reflection density ΔD2 of 0.2 or more in a range of cumulative illuminance of 10 mJ/cm$^2$ or more and less than 100 mJ/cm$^2$, and a change in reflection density ΔD3 of 0.2 or more in a range of cumulative illuminance of 100 mJ/cm$^2$ or more and 1,000 mJ/cm$^2$ or less, as measured at a wavelength of 365 nm when the ultraviolet-sensing sheet is irradiated with a high-pressure mercury lamp,
wherein the ultraviolet-sensing sheet comprises an ultraviolet-sensing layer comprising a capsule containing a photo-oxidant and a leuco dye capable of developing color by the photo-oxidant;
the mass ratio of the photo-oxidant and the leuco dye is 0.3 to 0.8:1; and
the leuco dye is present in an amount of 0.3 to 0.8 g per 1 m$^2$ of a surface area of the ultraviolet-sensing layer.

2. The ultraviolet-sensing sheet according to claim 1, wherein the photo-oxidant has a molar absorption coefficient ε of 2,000 or less at a wavelength of 350 nm and a molar absorption coefficient ε of 10,000 or more at a wavelength of 250 nm.

3. The ultraviolet-sensing sheet according to claim 2, wherein the capsule is a microcapsule.

4. The ultraviolet-sensing sheet according to claim 3, wherein the leuco dye is an aminoarylmethane.

5. The ultraviolet-sensing sheet according to claim 3, wherein the ultraviolet-sensing sheet has a cumulative illuminance of from 1 to 1,000 mJ/cm$^2$ as measured at a wavelength of 365 nm when the ultraviolet-sensing sheet is irradiated with a high-pressure mercury lamp.

6. The ultraviolet-sensing sheet according to claim 1, wherein the capsule is a microcapsule.

7. The ultraviolet-sensing sheet according to claim 6, wherein the leuco dye is an aminoarylmethane.

8. The ultraviolet-sensing sheet according to claim 7, wherein the ultraviolet-sensing sheet has a cumulative illuminance of from 1 to 1,000 mJ/cm$^2$ as measured at a wavelength of 365 nm when the ultraviolet-sensing sheet is irradiated with a high-pressure mercury lamp.

9. The ultraviolet-sensing sheet according to claim 1, wherein the leuco dye is an aminoarylmethane.

10. The ultraviolet-sensing sheet according to claim 1, wherein the ultraviolet-sensing sheet has a cumulative illuminance of from 1 to 1,000 mJ/cm$^2$ as measured at a wavelength of 365 nm when the ultraviolet-sensing sheet is irradiated with a high-pressure mercury lamp.

11. The ultraviolet-sensing sheet according to claim 1, further comprising a support having the ultraviolet-sensing layer thereon.

12. The ultraviolet-sensing sheet according to claim 11, wherein the support is a plastic film.

13. The ultraviolet-sensing sheet according to claim 11, further comprising a reflective layer between the support and the ultraviolet-sensing layer or on a surface of the support, the surface being away from the ultraviolet-sensing layer.

14. The ultraviolet-sensing sheet according to claim 13, wherein the reflective layer is disposed between the support and the ultraviolet-sensing layer.

15. The ultraviolet-sensing sheet according to claim 1, wherein the ultraviolet-sensing layer further comprises a reductant.

16. A method for manufacturing the ultraviolet-sensing sheet according to claim 1,
the method comprising applying to a support an ultraviolet-sensing layer composition comprising a capsule containing a photo-oxidant and a leuco dye capable of developing color by the photo-oxidant, and a mass ratio of the photo-oxidant and the leuco dye is 0.3 to 0.8:1; and
wherein the leuco dye is present in an amount of 0.3 to 0.8 g per 1 m$^2$ of the surface area of the support.

17. The method for manufacturing the ultraviolet-sensing sheet according to claim 16, wherein the change in reflection density ΔD1 is 0.25 or more, the change in reflection density ΔD2 is 0.25 or more, and the change in reflection density ΔD3 is 0.25 or more.

18. The method for manufacturing the ultraviolet-sensing sheet according to claim 16, wherein the mass ratio of the photo-oxidant and the leuco dye is 0.3 to 0.7:1.

19. The ultraviolet-sensing sheet according to claim 1, wherein the change in reflection density ΔD1 is 0.25 or more, the change in reflection density ΔD2 is 0.25 or more, and the change in reflection density ΔD3 is 0.25 or more.

20. The ultraviolet-sensing sheet according to claim 1, wherein the mass ratio of the photo-oxidant and the leuco dye is 0.3 to 0.7:1.

* * * * *